United States Patent [19]

Palmer et al.

[11] Patent Number: 4,820,857

[45] Date of Patent: Apr. 11, 1989

[54] α-BROMODIETHYLCARBONATE

[75] Inventors: Derek R. Palmer, Heswall; Robert G. Tyson, Prestatyn, both of Great Britain

[73] Assignee: Astra Lakemedel Aktiebolag, Sweden

[21] Appl. No.: 183,428

[22] Filed: Apr. 13, 1988

Related U.S. Application Data

[60] Continuation of Ser. No. 838,168, Mar. 10, 1986, abandoned, which is a division of Ser. No. 507,716, Jun. 23, 1983, Pat. No. 4,606,865.

[30] Foreign Application Priority Data

| Sep. 20, 1982 | [GB] | United Kingdom | 8226751 |
| Oct. 6, 1982 | [GB] | United Kingdom | 8228622 |
| Nov. 16, 1982 | [GB] | United Kingdom | 8232629 |
| Jan. 7, 1983 | [GB] | United Kingdom | 8300331 |

[51] Int. Cl.$^4$ .............................. C07C 69/96
[52] U.S. Cl. ............................ 558/277; 540/318; 540/336; 540/338
[58] Field of Search ........................ 558/277

[56] References Cited

U.S. PATENT DOCUMENTS

| 3,873,521 | 3/1975 | Ekstrom et al. | 540/318 |
| 4,072,677 | 2/1978 | Callander | 540/318 |

FOREIGN PATENT DOCUMENTS

| 309683 | 8/1973 | Austria . |
| 866093 | 10/1978 | Belgium . |
| 0054512 | 6/1982 | European Pat. Off. . |
| 2161420 | 7/1972 | Fed. Rep. of Germany . |
| 1795701 | 10/1973 | Fed. Rep. of Germany . |
| 1795702 | 10/1973 | Fed. Rep. of Germany . |
| 2423490 | 2/1975 | Fed. Rep. of Germany . |
| 3008257 | 9/1980 | Fed. Rep. of Germany . |
| 2141968 | 1/1973 | France . |
| 2387988 | 11/1978 | France . |
| 2482587 | 11/1981 | France . |
| 56-128736 | 3/1980 | Japan . |
| 7313549 | 10/1973 | Sweden . |
| 7505741 | 5/1975 | Sweden . |
| 1425571 | 2/1976 | United Kingdom . |
| 1426717 | 3/1976 | United Kingdom . |
| 1426869 | 3/1976 | United Kingdom . |
| 1427139 | 3/1976 | United Kingdom . |
| 1433131 | 4/1976 | United Kingdom . |
| 1443738 | 7/1976 | United Kingdom . |

OTHER PUBLICATIONS

Chemical Abstracts, 90:152209w, (1979).
Chemical Abstracts, 90:127547x, (1979).
Chemical Abstracts, 91:74633j, (1979).
Chemical Abstracts, 92:111279s, (1980).
Chemical Abstracts, 93:168262f, (1980).

Primary Examiner—Werren B. Lone
Assistant Examiner—Vera C. Clarke
Attorney, Agent, or Firm—Brumbaugh, Graves, Donohue & Raymond

[57] ABSTRACT

The novel compound α-bromodiethylcarbonate, novel methods for the preparation thereof, its use in the preparation of 1-ethoxycarbonyloxyethyl esters of penicillins and cephalosporins, and improvements in the method for preparing such esters.

1 Claim, No Drawings

α-BROMODIETHYLCARBONATE

This application is a continuation of Ser. No. 838,168, filed on Mar. 10, 1986, now abandoned, which in turn is a division of Ser. No. 507,716, filed June 23, 1983, now U.S. Pat. No. 4,606,865.

The present invention relates to the novel compound α-bromodiethylcarbonate, which with great advantage is used in preparing bacampicillin, and which in a more general sense is also used with great advantage in the preparation of the 1-ethoxycarbonyloxyethyl ester of 6-aminopenicillanic acid, penicillins and cefalosporins.

novel methods for the preparation of α-bromodiethylcarbonate.

novel intermediates in the preparation of α-bromodiethylcarbonate.

the use of α-bromodiethylcarbonate in the preparation of the 1-ethoxycarbonyloxyethyl ester of 6-aminopenicillanic acid, penicillins such as penicillin G, penicillin V and ampicillin, and cefalosporins.

improvements in the process for preparing 1-ethoxycarbonyloxyethyl esters of 6-aminopenicillanic acid, penicillins and cefalosporins.

Bacampicillin, or the 1-ethoxycarbonyloxyethyl ester of the 6-(D-(−)-α-phenylacetamido)penicillanic acid of the formula

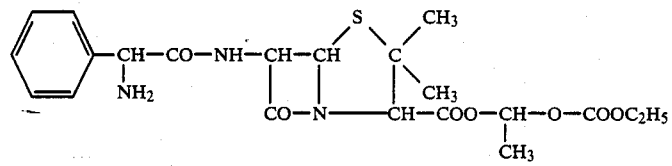
(I)

is an ampicillin ester which is extremely important from the therapeutic point of view since it is well absorbed when administered orally and gives much higher blood levels than ampicillin.

This ester is isolated in the form of a hydrochloride. On the basis of previous known processes (cf. Belgian Pat. No. 772723), bacampicillin hydrochloride can be synthesized by the two following methods:

(A) Reaction of potassium benzylpenicillin with α-chlorodiethylcarbonate in an aqueous solution of 70% dioxane in the presence of sodium bicarbonate. The 1-ethoxycarbonyloxyethyl ester of benzylpenicillin which is obtained is subjected to the reaction of removing the phenylacetic chain, via the iminochloride-iminoether, in order to obtain the 1-ethoxycarbonyloxyethyl ester of the 6-aminopenicillanic acid, which is isolated as the hydrochloride. By subsequent condensation of the latter intermediate with D-(−)-αphenylglycine, the compound according to formula I is obtained.

(B) Esterification reaction of the 6-(D-(−)-α-azido-α-phenylacetamido) penicillanic acid with α-chlorodiethylcarbonate in a polar solvent. Subsequently, by catalytic hydrogenation of the 1-ethoxycarbonyloxyethyl ester of the 6-(D-(−)-α-azido-α-phenylacetamido)penicillanic acid the compound according to formula I is obtained.

As one can see, these methods are rather complex since they involve the use of numerous raw materials and lengthy processing times.

THE INVENTION

An object of this invention is to provide a method of preparing the active substance concerned which is easier to carry out and industrially more advantageous.

The invention also provides the novel compound α-bromodiethylcarbonate, novel methods for the preparation thereof; novel intermediates in the preparation of α-bromodiethylcarbonate; the use of α-bromodiethylcarbonate in the preparation of the ethoxycarbonyloxyethyl ester of 6-aminopenicillanic acid, penicillins such as penicillin G, penicillin V and ampicillin, and cefalosporins; and improvements in the process for preparing ethoxycarbonyloxyethyl esters of 6-aminopenicillanic acid, penicillins and cefalosporins.

α-Bromodiethylcarbonate is used with great advantage as a reactant in these esterification processes. The use of α-bromodiethylcarbonate leads to particularly high yield and high purity of the final products such as bacampicillin.

The novel compound α-bromdiethylcarbonate of the invention, novel and inventive processes for the preparation thereof and its use in the preparation of the ethoxycarbonyloxyethyl esters of 6-aminopenicillanic acid, penicillins such as penicillin G, penicillin V and ampicillin, and cefalosporins, will now be described and exemplified in more detail.

This aspect of the invention is concerned with improvements in and relating to the preparation of α-bromodiethylcarbonate of the formula:

(II)

The alpha-bromo diethylcarbonate of the formula (II) may according to a further aspect of the invention, which is further dealt with later, be used in the synthesis of alpha(ethoxycarbonyloxy)-ethyl esters of 6-aminopenicillanic acid, penicillins and cefalosporins, for example the antibiotic bacampicillin. Alpha-bromodiethylcarbonate may thus advantageously be used in the preparation of the ethoxycarbonyloxyethyl esters of 6-aminopenicillanic acid, penicillin G, penicillin V and ampicillin.

According to the invention two novel and inventive processes, herebelow denoted process A and process B, are provided for the preparation of alpha-bromodiethylcarbonate of the formula II.

A. The first of these processes, process A, comprises the steps of:

(a) reacting an aldehyde of the formula $CH_3CHO$            (III)

with carbonyl bromide $COBr_2$            (IV)

to give an alpha-bromo-bromoformate of the formula:

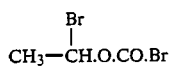

and;

(b) reacting the alpha-bromo-bromoformate of formula V with an alcohol of the formula $C_2H_5$—OH to yield the desired alpha-bromo-diethylcarbonate of the formula II.

Thus, the process A in accordance with the invention may be summarised by the reaction scheme:

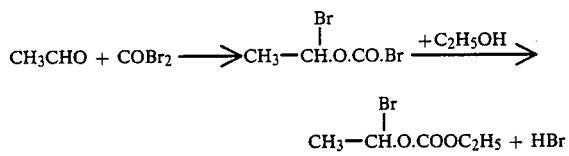

The alpha-bromo-bromoformate of the formula V is in it self a new compound and is provided as a further feature of the invention.

The reaction between the aldehyde, $CH_3CHO$, and carbonyl bromide is most suitably carried out in the presence of a catalyst which may be, for example, a tertiary amine (for example a tertiary aliphatic amine, a tertiary mixed alkyl/aryl amine or a tertiary aromatic amine), tertiary phosphine, amide, substitued urea or thiourea, phosphoric acid amide, tertiary oxonium or sulphonium salt, or a quaternary ammonium or phosphonium salt. Preferred examples of catalysts for use in the process A according to the invention include pyridine, dimethylformamide, tetra-n-butyl urea, hexamethyl-phosphoric-tri-amide and benzyltrimethyl ammonium bromide.

The catalyst is suitably used in an amount of from 0.05 to 0.5, preferably from 0.05 to 0.15, moles of catalyst per mole of aldehyde.

The reaction between the aldehyde and the carbonyl bromide is suitably carried out in the presence of a solvent which may be, for example, an aromatic hydrocarbon such as toluene or a halogenated hydrocarbon such as dichloromethane, carbon tetrachloride or chlorobenzene. The reaction between the aldehyde and the carbonyl bromide is suitably carried at a temperature of from $-40°$ to $120°$ C., preferably $0°-40°$ C. The carbonyl bromide will usually be used in molar excess with respect to the aldehyde, suitably in a molar excess of from 10 to 100%, preferably from 20 to 50%.

The intermediate alpha-bromo-bromoformate of formula V produced in step (a) of the process A of the invention need not be isolated prior to reaction with the alcohol $C_2H_5OH$ and, indeed, it is generally preferred not to do so. Thus, in accordance with a preferred embodiment of the invention, the reaction mixutre obtained from step (a) is freed of excess carbonyl bromide, for example by warming under reduced pressure or by purging with nitrogen. The crude alpha-bromo-bromoformate-containing reaction mixture is then reacted with an excess of the alcohol. The reaction may conveniently be effected by heating the mixture under reflux unitl the evolution of hydrogen bromide ceases or by adding a tertiary base to the mixture and, if necessary, warming it. Any residual catalyst from step (a) or its complex with carbonyl bromide does not appear to interfere with the subsequent reaction and, in some cases, appears beneficial.

The resultant crude alpha-bromocarbonate may conveniently be isolated from the reaction mixture by fractional distillation under reduced pressure.

Process A is illustrated in Examples 1 and 2, which are given by way of illustration only.

B. The second process, process B, of the invention for the preparation of α-bromodiethylcarbonate will now be described. Method B is exemplified in Examples 3, which is given by way of illustration only.

Process B of the invention is concerned with improvements in and relating to the preparation of α-bromodiethylcarbonate by a modification of the Finkelstein reaction, that is by reaction of an alkyl chloride or arylalkyl chloride (or a compound containing such a group) with an alkali metal bromide or alkali metal iodide to replace the chlorine substituent by a bromine or iodine substituent respectively; or by the reaction of an alkyl bromide or arylalkyl bromide (or a compound containing such a group) with an alkali metal iodide to replace the bromine substituent by an iodine substituent.

The Finkelstein reaction is useful since the resulting iodides are generally more reactive than the bromides which in turn are more reactive than the chlorides. In some cases only catalytic amounts of the alkali metal bromide or iodide are necessary and the resulting more reactive species is allowed to react with the desired substrate regenerating the alkali metal bromide or iodide, thus continuing the reaction.

Not all optionally substituted alkyl chlorides or arylalkyl chlorides undergo the reaction and, in particular, it has been found difficult to carry out the reaction with alpha-chloro esters and alpha-chlorocarbonates, that is compounds in which the chlorine atom is attached to a carbon atom which is, in turn, attached to either end of a group —C(O)—O—. An example of such an alpha-chlorocarbonate is α-chlorodiethylcarbonate, which is a known intermediate in the preparation of ethoxycarbonyloxyethyl esters of 6-aminopenicillanic acid and of penicillins as described above.

It has now been found, in accordance with the present invention, that this problem may be overcome by carrying out the reaction using a two-phase solvent system, one phase of which is water and the other is a water-immiscible organic solvent, in the presence of a phase transfer catalyst.

According to process B of the invention, therefore, there is provided a process for the preparation of α-bromodiethylcarbonate by reaction of α-chlorodiethylcarbonate with an alkali metal bromide, which process is characterized in that the reaction is carried out in a two-phase solvent system comprising water and a water-immiscible organic solvent in the presence of a phase transfer catalyst.

Suitable water-immiscible organic solvents for use in accordance with the invention include halogenated hydrocarbons, for example halogenated paraffins such as dichloromethane; and aromatic hydrocarbons such as toluene. Suitable phase transfer catalysts include quaternary ammonium salts, for example tetraalkyl ammonium salts such as cetyltrimethyl ammonium bromide and tetra-n-butyl ammonium hydrogen sulphate. The alkali metal bromide may, for example, be sodium, potassium, or lithium bromide, lithium bromide being preferred.

Thus, in process B of the invention, α-chlorodiethylcarbonate of the formula:

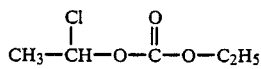

is reacted in a two-phase solvent system, one phase of which is water and the other is a water-immiscible organic solvent, with an alkali metal bromide of the formula R—Br (VII)

in which formula R is an alkali metal such as Na, K and Li, to the formation of the compound of the formula:

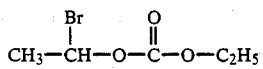

As noted above, the preferred alkali metal R is Li so that LiBr is a preferred reagent of the formula VII.

In connection with process B it has been found that lithium bromide may be used with advantage in a conventional Finkelstein reaction (i.e. one employing a single phase organic solvent system), for example to halogenate an alpha-chloro-carbonate. This method is exemplified in Example 4.

Accordingly, the present invention also provides, in accordance with a further embodiment thereof, a process for the preparation of α-bromodiethylcarbonate which comprises reacting α-chlorodiethylcarbonate with lithium bromide.

Suitable solvents for such a process include lower aliphatic alcohols, lower alphatic ketones, lower aliphatic ethers and lower aliphatic amides of formic acid.

The aspect of the invention which relates to the use of the novel compound α-bromodiethylcarbonate in the preparation of ethoxycarbonyloxyethyl esters of 6-aminopenicillanic acid (6-apa), penicillins and cefalosporins, will now be described.

In summary, this aspect of the invention comprises 1. the use of α-bromodiethylcarbonate in the preparation of the ethoxycarbonyloxyethyl esters of 6-aminopenicillanic acid, penicillins such as penicillin G, penicillin V and ampicillin, and cefalosporins, 2. a process for the preparation of the ethoxycarbonyloxyethyl ester of 6-aminopenicillanic acid, penicillins and cefalosporins, characterized by reacting 6-aminopenicillanic acid, the penicillin or the cefalosporin, or a salt thereof, with α-bromodiethylcarbonate to the formation of the ethoxycarbonyloxyethyl ester of the 6-aminopenicillanic acid, the penicillin and the cefalosporin, respectively, 3. the improvement in the esterification reaction between an α-halogendiethylcarbonate and 6-apa, a penicillin or a cefalosporin, which improvement comprises the use of a quaternary ammonium compound at the esterification step, whereby the said quaternary ammonium compound is present in an amount of 1-25, preferably 1-10% of the equimolar amount with respect to the amount of 6-apa, penicillin or cefalosporin.

The ethoxycarbonyloxyethyl ester in particular of 6-apa and of penicillin G are used as in known in the art in the preparation of any desired such semisynthetic penicillin ester by acylating the 6-$NH_2$ group after removing the side chain in e.g. the penicillin G ester obtained.

This aspect of the invention is concerned with improvements in and relating to the preparation of esters by the reaction of salts of carboxylic acids with α-bromodiethylcarbonate.

The reaction of metal salts of carboxylic acids with alkyl halides or arylalkyl halides to form esters is well known. However, yields are not particularly high and the reaction generally requires forcing conditions such as high temperatures and/or extended reaction times. These forcing conditions limit the synthetic utility of the reaction and its commercial applicability to heat sensitive and labile substances such as pyrethroids, prostaglandins, peptides, penicillins and cephalosporins.

The British patent specification No. 1443738 discloses the use of a quaternary ammonium salt of penicillins and cefalosporins in place of a metal salt thereof in the preparation of esters of penicillins and cefalosporins.

The preparation of the quaternary ammonium salt of the acid may be time-consuming and expensive. However, as is also disclosed in the British patent specification No. 1443738, it is not necessary to first prepare the quaternary ammonium salt of a penicillin or cefalosporin, but the reaction may be carried out by reacting a metal salt of the carboxylic acid, that is the 6-apa, penicillin or cefalosporin with the alkyl or arylalkyl halide in the presence of a quaternary ammonium salt, other than the salt of the carboxylic acid.

It has now been found, according to the present invention, that it is not necessary to employ the said quaternary ammonium salt in a stoichiometric amount with respect to the carboxylic acid, that is 6-apa, the penicillin or the cefalosporin, but that a less than stoichiometric amount with respect to the carboxylic acid, e.g. the 6-apa, penicillin or cefalosporin, will be sufficient.

According to the invention, therefore, there is provided a process for the preparation of an ethoxycarbonyloxyethyl ester of 6-apa, a penicillin or a cefalosporin by reaction of a metal salt or the 6-apa, penicillin or cefalosporin with α-halogendiethylcarbonate in the presence of a quaternary ammonium salt (other than a salt of the said carboxylic acid) whereby the quaternary ammonium compound is present in a less than stoichiometric amount with respect to the 6-apa, penicillin or cefalosporin.

In accordance with the invention, between 1% and 25% of an equivalent of the quaternary ammonium salt is used for each equivalent of the metal salt of the carboxylic acid, and more preferably between 1% and 10% of an equivalent of the quaternary ammonium salt is used.

The quaternary ammonium salt of the carboxylic acid is suitably prepared by reaction of a metal salt of the carboxylic acid with a quaternary ammonium salt of an acid other than said carboxylic acid, typically a mineral acid such as hydrochloric, hydrobromic or sulphuric acid.

Suitable metal salts of carboxylic acids for use in accordance with the present aspect of the invention (either as precursors for the carboxylic acid quaternary ammonium salt or as such) are alkali metal or alkaline earth salts such as sodium, potassium, lithium, magnesium and calcium salts. Suitable quaternary ammonium salts of acids other than the carboxylic acid (for use either as precursors for the carboxylic acids quaternary ammonium salts or as such) include for example tetraalkyl ammonium salts such as tetra-n-butyl ammonium bromide and cetyltrimethyl ammonium bromide and quaternary pyridinium salts such as cetyl-pyridinium bromide. Suitable halides include fluorides, chlorides, bromides and iodides, preferably activated fluorides or activated chlorides or bromides or iodides.

The esterification reaction in accordance with this aspect of the invention may be carried out in the presence or absence of a solvent. Suitable solvents include lower aliphatic alcohols, lower aliphatic ketones, lower aliphatic amides of formic acid and dimethyl sulphoxide. Alternatively, when no solvent is used, an excess of the ester forming halide may be used, particularly if this is a liquid at the temperature of the reaction.

In the previously described aspect of the invention which relates to the use of α-bromodiethylcarbonate in the preparation of ethoxycarbonyloxy ethyl esters of 6-apa, penicillins and cefalosporins, the use of catalyst is optional. Approximately equimolar amounts of the quaternary ammonium salt of the carboxylic acid and the ester forming halide may be used in the reaction. Preferably between 5% and 100% excess of the ester forming halide is used for each equivalent of the salt of the carboxylic acid used and more preferably an excess of between 20% and 60% of the ester forming halide is used.

The improvements in the esterification processes of the invention are particularly suitable for the preparation of the esters of 6-apa, penicillins and cephalosporins and thus, in accordance with a preferred embodiment of the invention the carboxylic acid may be of the formula:

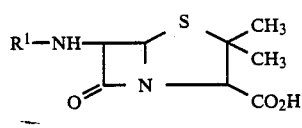

or

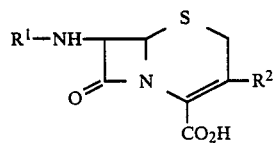

in which $R^1$ is a hydrogen atom or acyl group, particularly a substituted acetyl group such as a phenylacetyl; alpha-aminophenylacetyl; alpha-aminoparahydroxyphenylacetyl; phenoxyacetyl; alpha-carboxyphenylacetyl or alpha-carboxy-3-thienylacetyl group or, when the carboxylic acid is of the formula XII, a group:

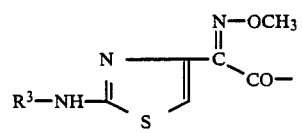

in which
$R^3$ is a hydrogen atom or an amino protecting group such as a benzyloxycarboxyl; trimethylsilyl or t-butyloxycarboxyl group, and
$R^2$ is a hydrogen atom; an alkyl group (e.g. a methyl group), a substituted alkyl group, e.g. a hydroxymethylene; alkoxy or arylkoxy methylene or acetoxy methylene group) or an acetoxy or substituted acetoxy group (e.g. an alkyl acetoxy, aryl acetoxy, or arylalkyl) acetoxy group or the group $C_6H_5.CHOH.CO-$).

In the preparation of esters of penicillins and cephalosporins according to the invention, the ester forming halide is an alpha-halodialkyl carbonate of the formula

$$CH_3-CH(X)-O-CO-O-CH_2-CH_3,$$

in which X is a chlorine, bromine or iodine atom, preferably a bromine atom.

In accordance with a preferred embodiment of the invention for the preparation of esters of penicillins and cephalosporins the quaternary ammoniium salt employed is tetra-n-butylammonium bromide.

In order that the invention may be well understood the following examples are given by way of illustration.

EXAMPLE 1

A mixture of acetaldehyde (44 g, 1 mole), carbon tetrachloride (300 ml) and freshly distilled carbonyl bromide (235 g, 1.25 mole) was cooled to 0° C. and maintained at this temperature by external cooling during the addition over a period of 1 hour of pyridine (11.9 g, 0.15 mole).

The mixture was allowed to warm up to ambient temperature and then heated to 50° C. and maintained at this temperature for a period of 3 hours during which time a precipitate formed.

Evaporation of the reaction mixture under reduced pressure at 50° C. gave a semi solid oily mass which readily dissolved in ethanol (92 g, 2 mole) on warming and heating under reflux. After heating under reflux for a further 2 hours, excess ethanol was removed in vacuo and the residue triturated with water (100 ml) and methylene dichloride (200 ml).

Separation of the organic layer and fractional distillation afforded pure ethyl alpha-bromo-ethyl-carbonate (130 g, 66% yield) having a boiling point of 90°-92° C. at 45 mms of mercury pressure and identical in all respects with an authentic specimen.

EXAMPLE 2

A mixture of acetaldehyde (44 g, 1 mole), dichloromethane (300 ml) and hexamethylphosphoric-tri-amide (17.9 g, 0.1 mole) was cooled to $-10°$ C. and freshly distilled carbonyl bromide (207 g, 1.1 mole) was gradually added over a period of 4 hours during which time the temperature was allowed to rise to 10° C.

The mixture was then heated under gentle reflux (ca. 40° C.) for 4 hours. While still under reflux, ethanol (69 g, 1.5 mole) was carefully added over a period of 1 hour and heating under reflux continued for a further 1 hour.

Fractional distillation of the resulting mixture afforded pure ethyl alpha-bromoethyl-carbonate directly (114 g, 58% yield).

The authenticity of the ethyl alpha-bronoethyl carbonate formed was confirmed by analysis and independent synthesis as follows.

Diethylcarbonate (118 g, 1.0 mole) was stirred and heated to between 110° C. and 120° C. and illuminated by a 150 watt tungsten filament lamp. Bromine (96 g, 0.6 mole) was added dropwise over a period of 3 to 4 hours and at such a rate that the mixture did not deepen beyond a pale orange colour.

After addition of bromine was complete, the mixture was cooled to ambient temperature and sodium bicarbonate (20 g) added.

Distillation and fractionation of the resulting mixture gave authentic ethyl alpha-bromo-ethyl carbonate (84.2 g, 70% yield) having a boiling point of 87°–88° C. at 40 mms of mercury pressure.

EXAMPLE 3

A mixture of lithium bromide (43 g, 0.5 m), ethyl alphachloroethyl carbonate (15.3 g, 0.1 m); water (100 ml), dichloromethane (100 ml) and cetyl trimethyl ammonium bromide (1.5 g) was stirred at ambient temperature for 24 hours. The aqueous layer was removed and replaced by a fresh solution of lithium bromide (26 g, 0.3 m) in water (40 ml) containing cetyl trimethyl ammonium bromide (1 g). After stirring for a further 24 hours during which time the temperature was raised to 35° C., the organic layer was separated, dried and vacuum distilled to afford after repeated fractionation the new compound, ethyl alpha-bromoethyl carbonate (15.0 g, 76% yield) having a boiling point of 90°–92° C. at 35 mms of mercury pressure.

Found: C 30.7; H 4.8; Br 40.1%; Calculated: C 30.5; H 4.6; Br 40.6%.

The NMR spectrum exhibited peaks as follows: 1.2–1.6 (3H, triplet): —CH$_2$.C$\underline{H_3}$; 2.0–2.2 (3H, doublet): —CH.C$\underline{H_3}$; 4.1–4.5 (2H, Quartet): —C$\underline{H_2}$.CH$_3$; 6.5–6.8 (1H, Quartet): —C$\underline{H}$.CH$_3$.

EXAMPLE 4

Lithium bromide (17.4 g, 0.2 m) was dissolved in dimethyl formamide (150 ml) and the mixture cooled to ambient temperature. Ethyl alphachloroethyl carbonate (30.5 g, 0.2 m) was added and the mixture stirred at ambient temperature for 24 hours. The precipitated lithium chloride was filtered off and the filtrate vacuum distilled to afford after careful re-fractionation, ethyl alpha-bromoethyl carbonate in 76% yield based upon recovered ethyl alphachloroethyl carbonate.

EXAMPLE 5

The authenticity of the foregoing new compound ethyl alpha-bromoethyl carbonate was confirmed by independent synthesis as follows:

A mixture of diethyl carbonate (35 g, 0.3 m) in carbon tetrachloride (50 ml) and alpha-azo-isobutyronitrile (AIBN) (0.1 g) was heated to gentle reflux and dibromodimethyl hydantoin (28.6 g, 0.1 m) was added in small aliquots over a period of 8 hours together with further additions of AIBN (8×0.05 g): care being taken to ensure that free bromine did not accumulate in the reaction mixture. At the end of the reaction the mixture was subjected to vacuum fractional distillation to afford pure ethyl alpha-bromoethyl carbonate (32.3 g, 82% yield) identical in all respects with the product of Examples 3 and 4.

EXAMPLE 6

Benzylpenicillin ethoxycarbonyloxyethyl ester

A mixture of potassium penicillin G (7.4 g, 20 mmole), ethyl alpha-chloro-ethyl carbonate (4.6 g, 30 mmole), tetra-n-butyl ammonium bromide (0.8 g, 2.5 mmole) and acetone (80 ml) were stirred and heated under gentle reflux for 4 hours. Excess acetone was removed under partial vacuum and the residue triturated with ice-cold water and methyl isobutylketone. Evaporation of the dried methyl isobutylketone under vacuum gave a semi-crystalline oil (3.8 g) which on trituration with ethanol deposited white crystals (0.9 g) of the alpha-(ethoxycarbonyloxy)-ethyl ester of penicillin G having a purity of 98–99% by HPLC.

Found: C 43.0; H 7.4; N 7.7%; Calculated: C 43.4; H 7.4; N 8.0%.

EXAMPLE 7

Benzylpenicillin ethoxycarbonyloxyethyl ester

The foregoing experiment of Example 11 was repeated using ethyl alpha-bromo-ethyl carbonate (5.9 g, 30 m mole) instead of ethyl alpha-chloro-ethyl carbonate, whereon there was obtained, on evaporation of the methyl isobutyl ketone, 6.0 g of a semicrystalline oil. Trituration of this oil with warm ethanol and then cooling afforded white crystals (2.5 g, 35% yield) of the alpha-(ethoxycarbonyloxy)-ethyl ester of penicillin G.

EXAMPLE 8

Benzylpenicillin ethoxycarbonyloxyethyl ester

Potassium benzylpenicillinate (25.08 g, 66.7 mmol) sodium bicarbonate (0.50 g, 6.0 mmol), and tetrabutylammonium bromide (2.15 g, 6.67 mmol) were carefully stirred in methylene chloride (41 ml) and warmed to 40° C. When this temperature was reached α-bromodiethyl carbonate 17.16 g, 86.7 mmol) was added and the slurry was stirred for 4.0 hours. Water (30 ml) was added, followed by a mineral acid to a pH of approx. 5. The mixture was stirred for approx. 4 hours, during which time sodium hydroxide (4%) was added in order to maintain pH between 2.5–3.0. Methylene chloride (50 ml) was then added and the mixture was allowed to separate for a few minutes. The organic phase was washed with water (65 ml) and was then evaporated under reduced pressure. The oily product thus obtained was dissolved in methylene chloride (100 ml) and was evaporated again. The remaining oil was dissolved in methylene chloride to a total volume of 100 ml.

HPLC-analysis of the methylene chloride solution showed a yield of benzylpenicillin ethoxycarbonyloxyethyl ester of 96–97%.

EXAMPLE 9

Benzylpenicillin ethoxycarbonyloxyethyl ester

Potassium benzylpenicillinate (5.02 g, 13.3 mmol) and potassium bicarbonate (2.99 g, 38.3 mmol) in dimethyl sulfoxide (13.5 ml) were carefully stirred in an ice-bath. α-bromodiethyl carbonate (3.70 g, 18.6 mmol) was added over a period of 30–40 min using a syringe pump. Stirring was continued while keeping the reaction mixture in the ice-bath. HPLC-analyses showed that a yield of about 70% of the benzylpenicillin ethoxycarbonyloxyethyl ester was obtained within 5–10 min.

EXAMPLE 10

Benzylpenicillin ethoxycarbonyloxyethyl ester

Potassium benzylpenicillinate (47.03 g, 125 mmol) sodium bicarbonate (0.94 g, 11 mmol), and tetrabutylammonium bromide (2.01 g, 6.25 mmol) were carefully stirred in acetone (77 ml) and warmed to 40° C. When this tempereature was reached α-bromodiethyl carbonate (26.06 g, 131 mmol) was added and the slurry was stirred for 4.5 hours. Water (56 ml) was added, followed by a mineral acid to a pH of approx. 5. The mixture was stirred for approx. 3 hours, during which time sodium hydroxide (4%) was added in order to maintain pH between 4.5–4.8. Butyl acetate (100 ml) was then added and the mixture was allowed to separate for a few minutes. The organic phase was washed with water (80 ml) and then evaporated under reduced pressure. The remaining oily product was dissolved in methylene chloride to a total volume of 250 ml.

HPLC-analysis of the methylene chloride solution showed a yield of benzylpenicillin ethoxycarbonyloxyethyl ester of 98–99%.

The compound α-bromodiethylcarbonate and its use in the preparation of the 1-ethylcarbonyloxyethyl ester of ampicillin is disclosed in the Italian patent application No. 22141A/82 filed on June 29, 1982, in the name of Biochimica Opos Srl. The content of the said Italian patent application is hereby incorporated by reference in the present application. Also the content of the corresponding U.S. patent application titled "Novel synthesis route for bacampicillin" in the name of Luigi Ratti Ser. No. 507,717, filed Dec. 21, 1984 and which is based on and claims priority from the said Italian patent application is hereby incorporated by reference in the present specification.

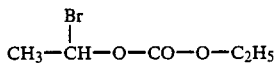

What we claim is:

1. The compound of the formula